United States Patent [19]

Umezawa et al.

[11] 3,956,274

[45] May 11, 1976

[54] NEW COMPOUND 6'-DEOXY-6'-SUBSTITUTED OR UNSUBSTITUTED AMINO-LIVIDOMYCINS AND THE PRODUCTION THEREOF

[75] Inventors: Sumio Umezawa; Hamao Umezawa, both of Tokyo; Osamu Tsuchiya, Yokohama; Isamu Watanabe, Murayama, all of Japan

[73] Assignee: Zaidan Hojin Biseibutsu Kagaku Kenkyu Kai, Tokyo, Japan

[22] Filed: Mar. 5, 1974

[21] Appl. No.: 448,250

[30] Foreign Application Priority Data

Mar. 13, 1973 Japan............................... 48-28513

[52] U.S. Cl............................ 260/210 AB; 424/180
[51] Int. Cl.².......................................... C07H 15/22
[58] Field of Search.... 260/210 AB, 210 K, 210 NC

[56] References Cited

UNITED STATES PATENTS

| | | | |
|---|---|---|---|
| 3,350,387 | 10/1967 | Vanderhaeghe | 260/210 K |
| 3,669,838 | 6/1972 | Shier et al. | 260/210 AB |
| 3,753,973 | 8/1973 | Umezawa et al. | 260/210 K |
| 3,808,198 | 4/1974 | Naito et al. | 260/210 AB |

*Primary Examiner*—Johnnie R. Brown
*Attorney, Agent, or Firm*—James C. Haight

[57] ABSTRACT

Lividomycin B derivatives having enhanced antibacterial activity are provided; the 6'-deoxy-6' substituted or unsubstituted amino lividomycins are prepared by masking the functional groups other than the 4' - and 6' -hydroxyl groups, converting the 6' hydroxyl group to an amino group and then removing the remaining protective groups.

9 Claims, No Drawings

COMPOUND 6'-DEOXY-'-SUBSTITUTED OR UNSUBSTITUTED AMINO-LIVIDOMYCINS AND THE PRODUCTION THEREOF

This invention relates to new derivatives of lividomycin and more particularly 6'-deoxy-6'-substituted or unsubstiuted amino-lividomycins new substances which are useful in the therapeutic treatment of infections by gram-positive and gram-negative bacteria, including drug-resistant bacteria. This invention further relates to a process for the production of said 6'-deoxy-6'-substituted or unsubstituted amino-lividomycins.

Aminoglycosidic antibiotics such as kanamycins, neamines and ribostamycin e.g. (see "The Journal of Antibiotics" Vol. 23, No. 3, pp. 155–161 and No. 4, pp. 173–183 (1970), are known and these antibiotics have been used widely as valuable chemotherapeutic agents. However, some drug-resistant strains of bacteria which are resistant to these known aminoglycosidic antibiotics have occurred in recent years. In this situation, the mechanism of resistance of these drug-resistant bacteria to the known aminoglycosidic antibiotics has been studied. For instance, one of the inventors, H. Umezawa et al. have found that some strains of gram-negative bacteria carrying R factor, *Staphylococcus aureus* and *Pseudomonas aeruginosa* isolated from patients, are resistant to kanamycins and that these kanamycin-resistant strains have as a mechanism of resistance the production of an enzyme capable of phosphorylating the 3'-hydroxyl group of kanamycins and inactivate the kanamycins under the action of the phosphotransferase (see the "Science" Vol. 157, page 1559 (1967)).

On the basis of this finding, H. Umezawa et al. have prepared synthetically 3'-deoxykanamycin wherein the 3'-hydroxyl group of the kanamycin molecule is removed therefrom, as well as 3',40'-dideoxykanamycin B, 3', 4'-dideoxyneamine and 3',4'-dideoxyribostamycin as described in the "Journal of Antibiotics" Ser. A. Vol. 24, pp. 274–275 (1971); Vol. 24, pp. 485–487; Vol. 24, pp. 711–712 (1971) and Vol. 25, pp. 613–617 (1972). 3'-Deoxykananmycin; 3', 4'-dideoxykanamycin B; and 3', 4'-dideoxyneamine are actually effective against the above-mentioned kanamycin-resistant strains, but 3', 4'-dideoxyribostamycin can be inactivated by some strains producing the phosphotransferase. Besides, these deoxy derivatives of the aminoglycosidic antibiotics have been found to be inactive against another class of kanamycin-resistant strains such as *Escherichia coli* K-12, R-5 and *Pseudomonas aeruginosa* GN-315, etc., which have been isolated from patients and which produce an enzyme capable of acetylating the 6'-amino group of the aforesaid deoxy derivatives. Accordingly, H. Umezawa et al. have synthetized 6'-N-alkylated derivatives of the aforesaid deoxy compounds which are active against the *E. coli* K-12, R-12, R-5 and *P. aeruginosa* GN-315; (see the "Journal of Antibiotics" Vol. 25, No. 12, pp. 743–745 (1972).

Lividomycin B is one of the known aminoglycosidic antibiotics e.g. (see "The Journal of Antibiotics" Vol. 24, pp. 333–346 (1971); and Vol. 25, pp. 149–150 (1972). Lividomycin B itself has neither the 3'-hydroxyl group nor the 6'-amino group in the molecule thereof and is active against the kanamycin-resistant bacteria as mentioned above. However, it is desired to enhance further the antibacterial activity of lividomycin B against the kanamycin-sensitive bacteria as well against as the kanamycin-resistant bacteria.

An object of this invention is to provide new and useful derivatives of lividomycin B which have enhanced antibacterial activity against the kanamycin-sensitive bacteria as well as the kanamycin-resistant bacteria. A further object of this invention is to provide a synthetic process for producing such a new and useful derivative of lividomycin B, which is carried out in a facile way and in a favorable yield of the desired product. Other objects of this invention will be clear from the following descriptions.

We have made our extensive research to modify the hydroxyl and amino groups of lividomycin B molecule in various ways in an attempt to obtain such a new derivative of lividomycin B which exhibits a usefully enhanced antibacterial activity. As a result, we have now found that to replace the 6'-hydroxyl group of lividomycin B with an amino group imparts lividomycin B with significantly improved antibacterial activity against the kanamycin-sensitive and -resistant bacteria. We have also found that a 6'-deoxy-6'-substituted or unsubstituted amino-lividomycin B can be produced by protecting the functional groups other than the 4'- and 6'-hydroxyl group of lividomycin B by acylating, alkoxycarbonylating, aryloxycarbonylating, arylmethoxycarbonylating, alkylidenating or arylidenating all the amino groups of lividomycin B; and converting the 6'-hydroxyl group of the protected derivative of lividomycin B into an amino group, substituted or unsubstituted, in a known manner, and then removing the remaining protective groups to produce the desired 6'-deoxy-6'-substituted or unsubstituted amino-lividomycin B.

According to a first aspect of the present invention, therefore, there is provided as a new and useful compound a 6'-deoxy-6'-substituted or unsubstituted amino-lividomycin B of the general formula: I

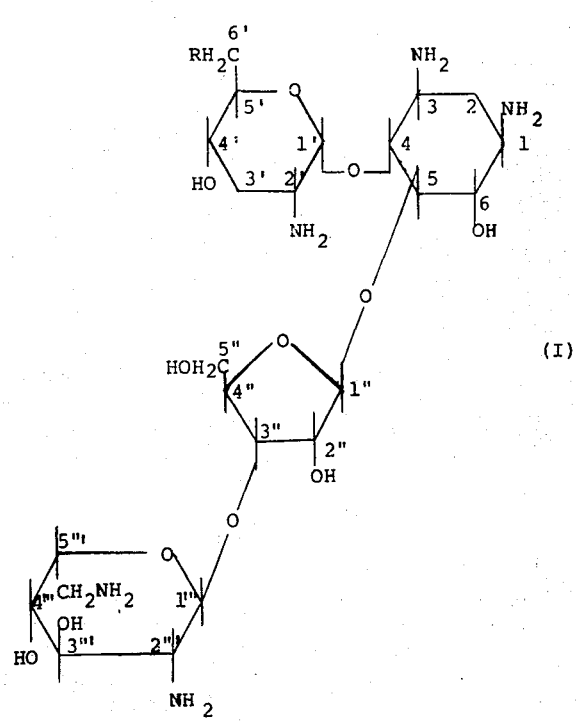

wherein R is the amino group —$NH_2$ or an alkylamino group of the formula $NHR_1$ in which $R_1$ is an alkyl group of 1-4 carbon atoms or the 2-hydroxyethyl group, and the acid-addition salts of said lividomycin B derivative.

As examples of the new compounds of the above formula (I) according to the present invention are mentioned the following specific compounds:

(1) 6'-Amino-6'-deoxylividomycin B (in formula I: R=$NH_2$).
(2) 6'-Deoxy-6'-methylaminolividomycin B (in the formula I: R=$NHCH_3$).
(3) 6'-Deoxy-6'-(2-hydroxyethylamino) lividomycin B (in formula I: R=$NHCH_2CH_2OH$).

Examples of the pharmaceutically acceptable acid-addition salts of the new substances of the general formula (I) according to this invention include the hydrochloride, sulfate, phosphate, acetate, maleate, fumarate, succinate, tatrate, oxalate, citrate, methanesulfonate, ethanesulfonate and the like.

Physical and biological properties of the new substances of this invention are described below.

The compounds of formula (I) according to the present invention exhibit not only an antibacterial activity as high as or more than that of their parent substance lividomycin B against various gram-positive and gram-negative bacteria which are sensitive to the lividomycin B, but they also exhibit a high antibacterial activity against the kanamycin-resistant strains of *Staphylococcus aureus*, *Escherichaia coli* and *Pseudomonas aeruginosa* as well as against *Klebsiella pneumoniae* and *Salmonella typhosa*.

The minimum inhibitory concentrations (mcg/ml) of 6'-amino-6'-deoxylividomycin B, 6'-deoxy-6'-methylaminolividomycin B and 6'-deoxy-6'-(2-hydroxyethylamino) lividomycin B against various microorganisms were determined according to a standard serial dilution method using nutrient agar incubation medium at 37°C, the estimation being effected after 18 hours incubation except for Mycobacterium smegmalis ATCC 607, in which the estimation being effected after 48 hours incubation. The minimum inhibitory concentrations (mcg/ml) of neomycin and lividomycin B were also determined in the same manner they also for comparison. Antibacterial spectra of these substances are shown in the following table.

TABLE 1

Antibacterial spectra of 6'-amino-6'-deoxylividomycin B (ALVB), 6'-deoxy-6'-methylaminolividomycin B (MALVB), 6'-deoxy-6'-(2-hydroxyethylamino)lividomycin B (HALVB), neomycin (NM) and lividomycin B (LVB).

| Test organisms | | | ALVB | MALVB | HALVB | NM | LVB |
|---|---|---|---|---|---|---|---|
| Staphylococcus aureus FDA 209 P | | | <0.20 | <0.20 | 0.39 | 0.39 | 1.56 |
| Sarcina lutea PCI 1001 | | | 0.78 | 6.25 | 25 | 0.78 | 1.56 |
| Bacillus subtilis NRRL B-558 | | | <0.20 | <0.20 | <0.20 | <0.20 | <0.20 |
| Klebsiella pneumoniae | PCI 602 | | 0.78 | 0.78 | 0.78 | 0.78 | 1.56 |
| " | type 22 No. 3038 | | 1.56 | 1.56 | 3.12 | >100 | 6.25 |
| Salmonella typhosa T-63 | | | 0.39 | 0.78 | 1.56 | 0.78 | 0.78 |
| Escherichia coli | NIHJ | | 0.78 | 3.12 | 3.12 | 1.56 | 3.12 |
| " | K-12 | | 0.78 | 0.78 | 1.56 | 1.56 | 1.56 |
| " | " | R-5 | 0.39 | 1.56 | 1.56 | 0.78 | 1.56 |
| " | " | ML 1629* | 50 | >100 | >100 | 100 | >100 |
| " | " | ML 1630 | 50 | >100 | >100 | >100 | >100 |
| " | " | ML 1410 | 1.56 | 3.12 | 3.12 | 6.25 | 6.25 |
| " | " | R 81 | 100 | >100 | >100 | >100 | >100 |
| " | " | LA 290 R 55* | 1.56 | 1.56 | 1.56 | 0.78 | 3.12 |
| " | " | " R 56 | 0.39 | 1.56 | 0.78 | 0.78 | 3.12 |
| " | " | " R 64 | 0.78 | 0.78 | 1.56 | 0.39 | 3.12 |
| " | " | C 600 R135 | 0.78 | 0.78 | 1.56 | 0.78 | 3.12 |
| " | " | W 677 | 0.78 | 0.78 | 1.56 | 0.78 | 3.12 |
| " | " | JR 66/W 677* | 1.56 | 3.12 | 6.25 | >100 | 6.25 |
| " | " | J 5 R 11-2 | 25 | 100 | >100 | 50 | >100 |
| Pseudomonas aeruginosa | A 3 | | 1.56 | 3.12 | 6.25 | 25 | 6.25 |
| " | No.12 | | 0.78 | 0.78 | 0.78 | 3.12 | 25 |
| " | GN 315* | | 25 | 3.12 | 12.5 | 100 | 50 |
| " | TI-13-1 | | 100 | >100 | >100 | >100 | >100 |
| " | 99 | | 1.56 | 25 | 25 | 50 | 100 |
| Proteus rettgeri | GN 311 | | 25 | 25 | 50 | 50 | 1.56 |
| " | GN 466 | | 3.12 | 12.5 | 6.25 | 3.12 | 3.12 |
| Mycobacterium smegmatis ATCC 607** | | | <0.20 | <0.20 | <0.20 | <0.20 | 0.39 |

In the above table, the mark * denotes the strain is a drug-resistant strain of patient-origin.
The mark ** shows that the incubation was made for 48 hours.

From the above table, it is seen that the new compounds of formula (I) of the present invention have remarkably higher antibacterial activity against some particular bacteria species or strains than the parent substance lividomycin B.

The new compounds of the formula (I) according to this invention are of a lower toxicity to animals and men, as shown by the fact that they show an $LD_{50}$ value of about 50 mg/kg upon intravenous injection of the compound in mice. In addition, the new compounds of this invention exhibit a high antibacterial activity against various gram-positive and gram-negative bacteria, including the kanamycin-resistant strains, so that the new compounds of this invention may be useful in treatment of infections by gram-positive and gram-negative bacteria. The compounds of this invention may be administered orally, intraperitoneally, intravenously or intramuscularly using any pharmaceutical form known to the art for such administration and in a similar manner to kanamycins. For instance, compounds of formula (I) of this invention may be administered orally using any pharmaceutical form known to the art for such oral administration. Examples of pharmaceutical forms for oral administration are powders, capsules, tablets, syrup, and the like. A suitable dose of the compounds for the effective treatment of bacterial infections is in a range of 0.25–2 g per person a day when given orally. It is preferred that said dose should be orally administered in three to four aliquots per day. The compounds of this invention may also be administered by intramuscular injection at a dosage of 50–200 mg. per person once or twice a day. Moreover, the compounds of the invention may be formulated into an ointment for external application which contains the compounds of this invention at a concentration of 0.5–5% by weight in mixture with a known ointment base such as polyethylene glycol.

We have further found the following: When lividomycin B of the formula:

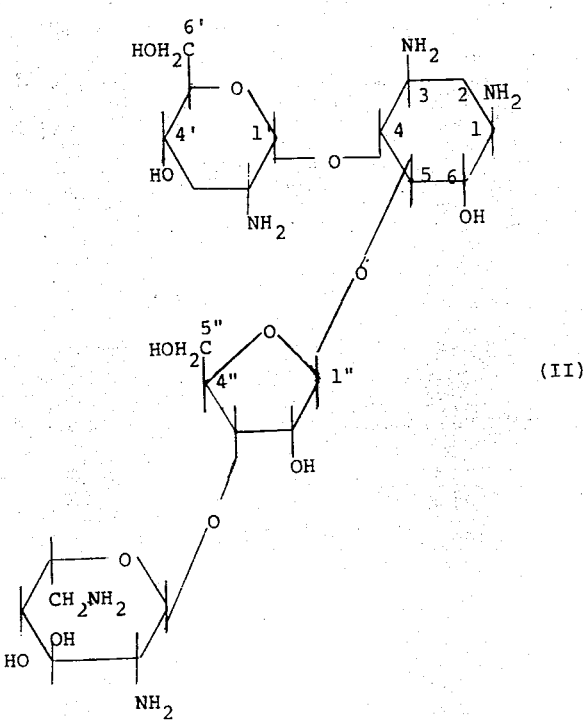

is used as the starting material and all the amino groups of lividomycin B are protected by acylation, alkoxycarbonylation, arylmethoxycarbonlya, orylmethoxycarbonylation, alkylidenation or arylidenation in a known manner, affording a penta-N-protected derivative of the general formula:

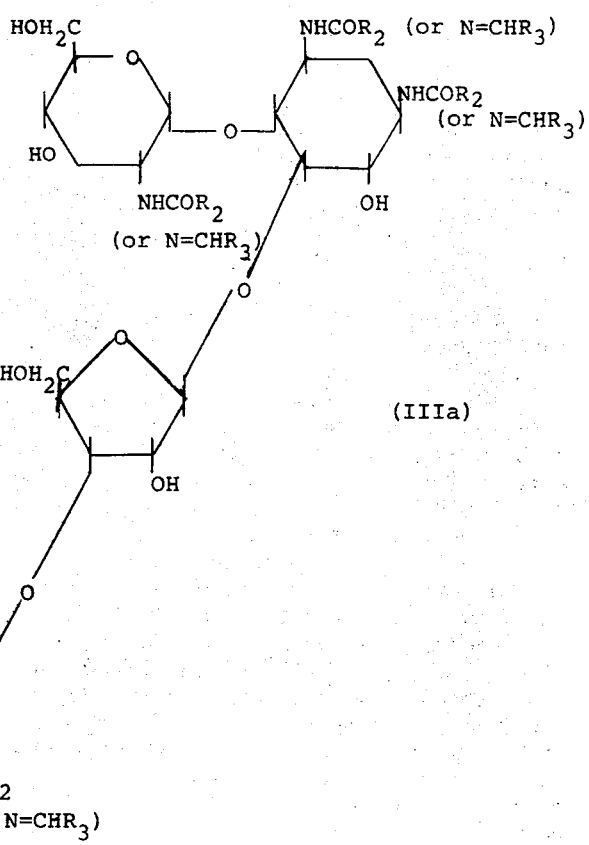

wherein $R_2$ is a hydrogen atom, an alkyl group, aryl group, alkoxy group, aryloxy group or an arylmethoxy group such as benzyloxy; and $R_3$ is an alkyl group or aryl group, the 6'-hydroxyl group of said penta-N-protected derivative of the formula (IIIa) can be immediately converted either into amino group —$NH_2$ by sulfonylating or halogenating said 6'-hydroxyl group and then treating the resultant 6'-sulfonic ester group or 6'-halo group with a metal azide followed by hydrogenation of the azide group so formed, or into an amino group —$NHR_1$ (which may be substituted or unsubstituted) by sulfonylating or halogenating said 6'-hydroxyl group and then reacting the resultant 6'-sulfonic ester group or 6'-halo group with ammonia, a lower alkylamine or ethanolamine. When the sulfonylation or halogenation of the 6'-hydroxyl group is effected, however, the 5''-hydroxyl group can be sulfonylated or halogenated, too, because the 5''-hydroxyl group is a primary hydroxyl group and has a reactivity as high as that of the 6'-hydroxyl group as long as the 5''-hydroxyl group is not blocked. The 5''-sulfonic ester or 5''-halo group so occasionally formed is susceptible to the subsequent reaction with a metal azide or with ammonia or an amine, leading to the formation of a 5''-deoxy-5''-amino-derivative of lividomycin B which is undesired for the object of the present invention. Clearly this reduces the yield of the desired product of the formula (I), and it is seen that the formation of the 5''-sulfonylated or 5''-halogenated derivative of lividomycin B should be suppressed as much as possible and the penta-N-protected derivative of lividomycin B of the formula (IIIa) should be sulfonylated or halogenated at the 6'-hydroxyl group thereof preferentially as much as possible in order to obtain the desired 6'-deoxy-6'-amino-lividomycin B of the formula (I) in an acceptably high yield.

We have now found that a preferential 6'-monosulfonylation or 6'-mono-halogenation of the 6'-hydroxyl group of the penta-N-protected lividomycin B derivative of the formula (IIIa) can be obtained by protecting firstly both the 4'- and 6'-hydroxyl groups at the same time by acetalation or ketalation in such a manner to prepare a 4',6'-O-protected derivative of the general formula:

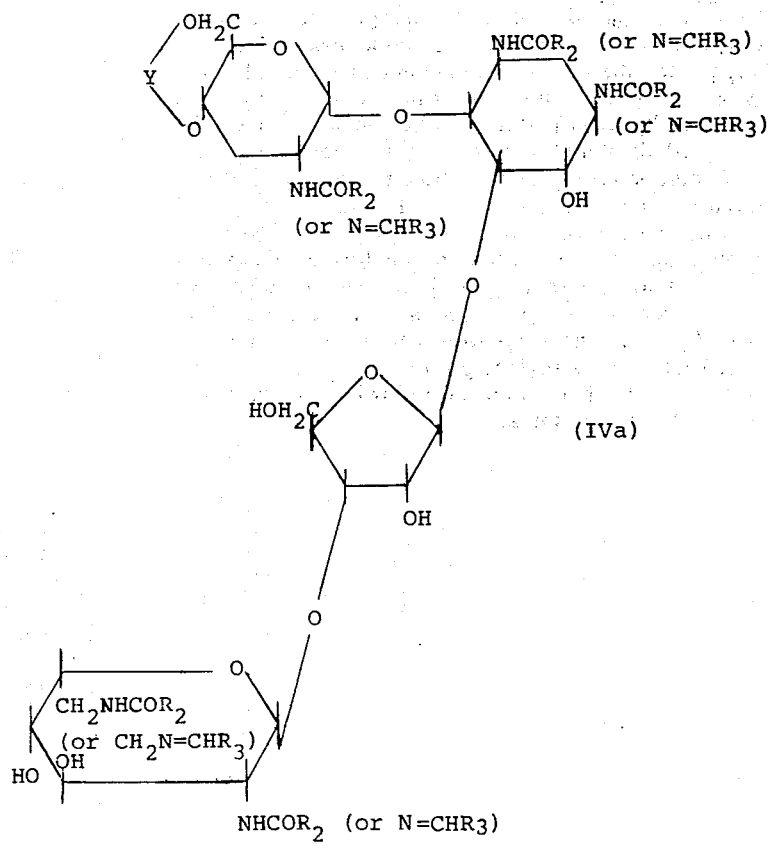

(IVa)

wherein $R_2$ and $R_3$ have the same meanings as defined above and Y is a cyclohexylidene group or tetrahydropyranyl group of the formula

or a group of the formula

in which P and P' each is a hydrogen atom or an alkyl group or an aryl group, then protecting all or a part of the remaining hydroxyl groups of the 4',6'-O-protected derivative of the formula (IVa) by acylation, benzylation or tetrahydropyranylation in a known manner to prepare a protected derivative of the general formula:

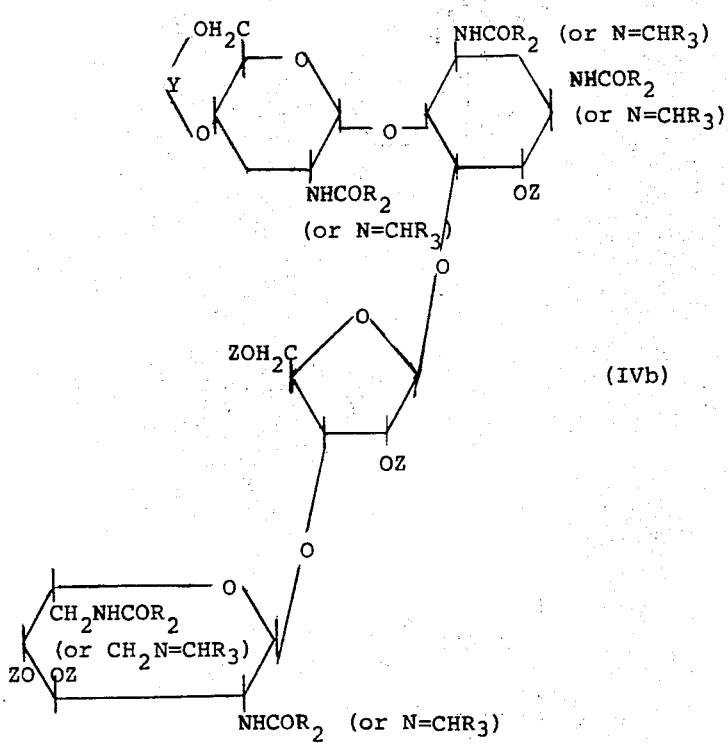

(IVb)

wherein $R_2$, $R_3$ and Y have the same meanings as defined above; and Z is a hydrogen atom, an acyl group, benzyl group or tetrahydropyranyl group of the formula

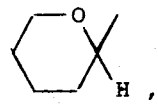

then removing the 4′,6′-hydroxyl-protecting group -Y- from the derivative of the formula (IVb), and sulfonylating or halogenating the 6′-hydroxyl group so liberated to prepare a derivative of the general formula:

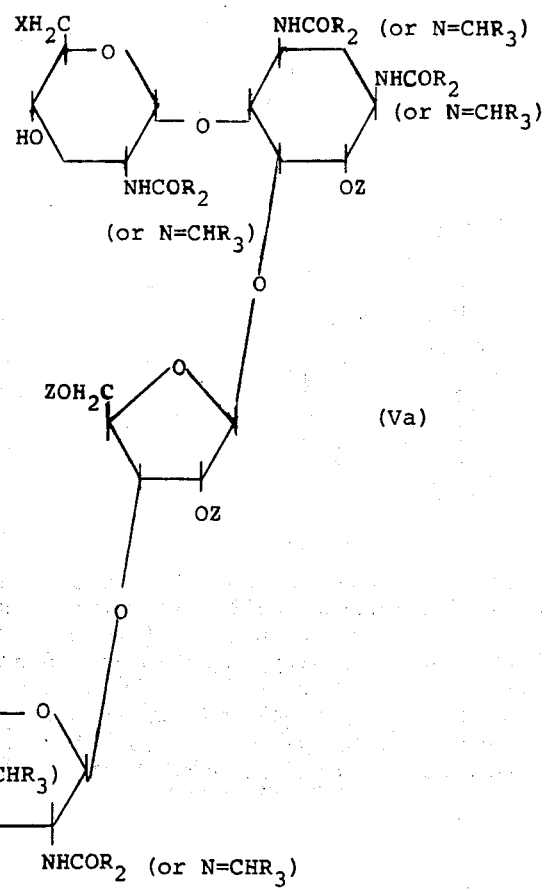

(Va)

wherein $R_2$, $R_3$ and Z have the same meanings as defined above; and X is an alkylsulfonyl group, an arylsulfonyl group or a halo group. The group X at the 6'-position of the derivative of the formula (Va) may subsequently be converted into amino group $-NH_2$ in a facile way by reacting with a metal azide such as sodium azide and hydrogenating the resultant azide group $-N_3$ with hydrogen-palladium or hydrogen-Raney nickel, or alternatively the group X may also readily be converted into amino group $-NH_2$, or a lower alkylamino group or 2-hydroxyethylamino group by reacting with ammonia or a lower alkylamine or ethanolamine.

According to a second aspect of the present invention, therefore, there is provided a process for the production of a 6'-deoxy-6'-substituted or unsubstituted amino-lividomycin B of the formula:

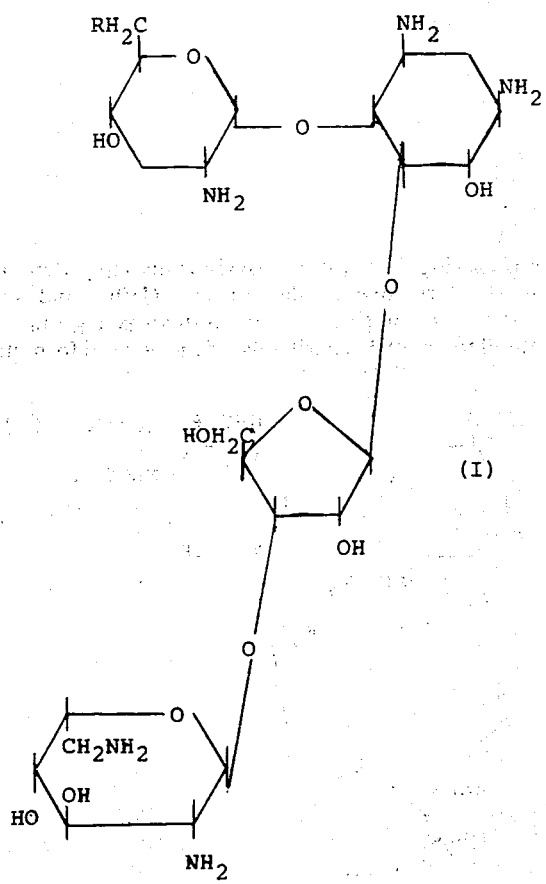

(I)

wherein R is amino group $-NH_2$ or an alkylamino group of the formula $-NHR_1$ in which $R_1$ is an alkyl group of 1–4 carbon atoms or 2-hydroxyethyl group, which comprises protecting all the amino groups of lividomycin B by acylation, alkoxycarbonylation, aryloxycarbonylation, arylmethoxycarbonylation, alkylidenation or arylidenation to prepare a penta-N-protected derivative of the formula:

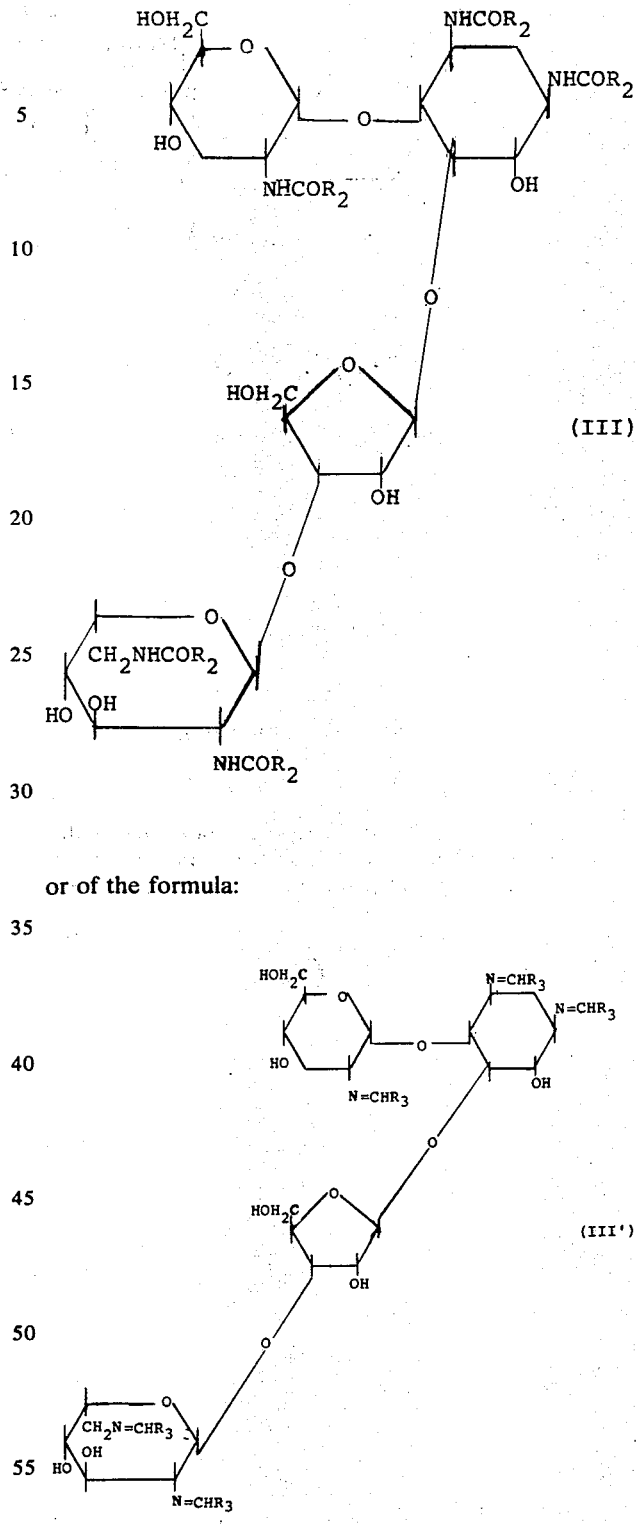

(III)

or of the formula:

(III')

wherein $R_2$ is a hydrogen atom, an alkyl group (for example, an alkyl group of 1–4 carbon atoms, such as methyl, ethyl, butyl, propyl and pentyl), an aryl group (for example, phenyl), an alkoxyl group (for example, an alkoxyl group of 1-6 carbon atoms, such as ethoxyl, t-butoxyl and t-amyloxyl), an aryloxy group (for example, phenoxy) or an arylmethoxy group (for example, benzyloxy and p-nitrobenzyloxy); and $R_3$ is an alkyl group (for example, an alkyl group of 1–6 carbon atoms, such as methyl, ethyl, propyl, isopropyl, butyl and pentyl) or an aryl group (for example, phenyl, tolyl, p-methoxyphenyl or o-hydroxyphenyl), then acetalating or ketalating the 4'- and 6'-hydroxyl groups of the penta-N-protected derivative of the formula (III) or (III') to prepare a 4',6'-O-protected derivative of the formula:

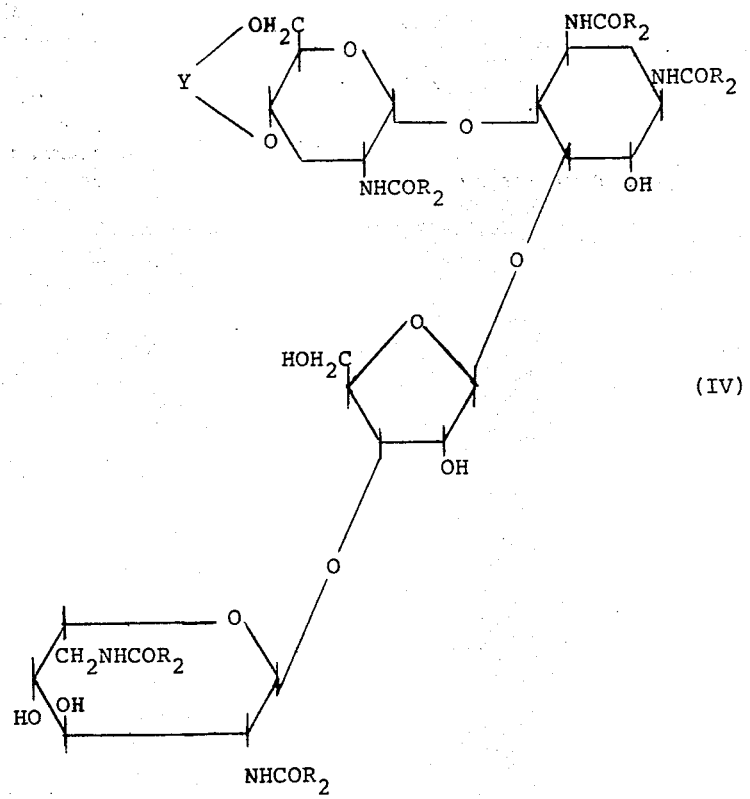

(IV)

or of the formula:

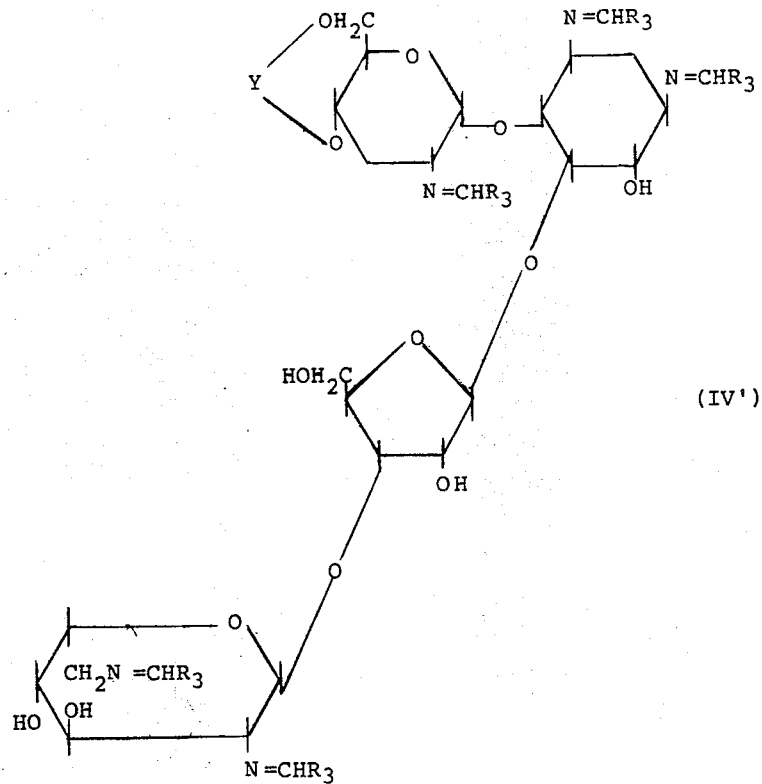

(IV')

wherein $R_2$ and $R_3$ have the same meanings as defined in the above; and Y is cyclohexylidene group or tetrahydropyranyl group of the formula:

or a group of the formula:

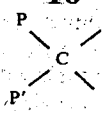

in which P and P' are each a hydrogen atom or an alkyl group (for example, an alkyl group of 1–4 carbon atoms, such as methyl, ethyl, propyl and butyl) or an aryl group (for example, phenyl, tolyl, p-methoxyphenyl, o-hydroxyphenyl) then protecting all or a part of the remaining hydroxyl groups of the 4',6'-O-protected derivative of the formula (IV) or (IV') by acylation, benzylation or tetrahydropyranylation to prepare a protected derivative of the formula:

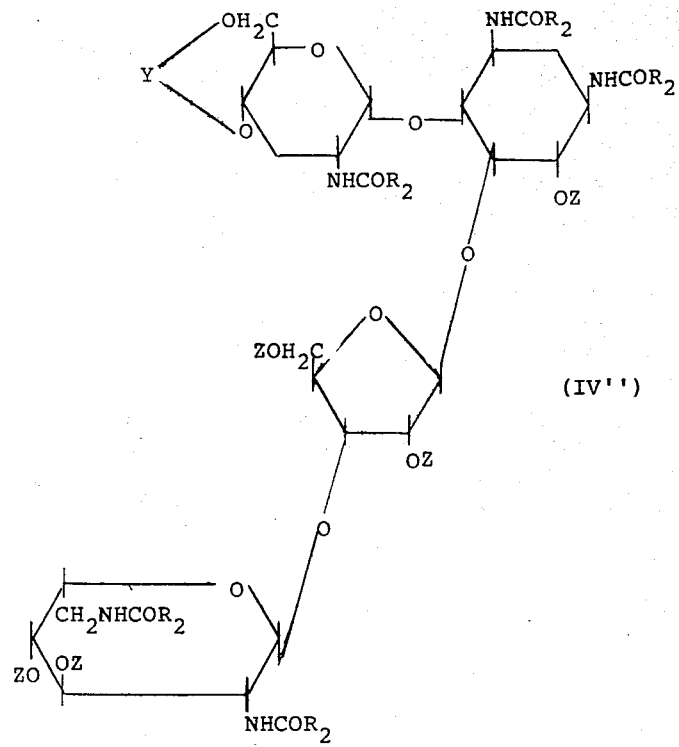

(IV'')

or of the formula:

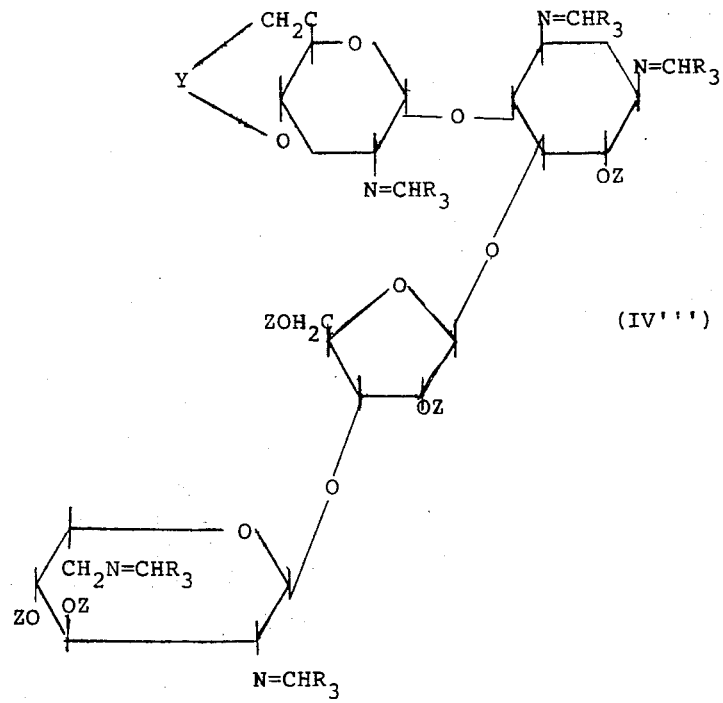

(IV''')

wherein $R_2$, $R_3$ and Y have the same meanings as defined above; and Z is a hydrogen atom, an acyl group (for example, an alkanoyl group of 2–5 carbon atoms such as acetyl, propionyl and butyryl), benzyl group or tetrahydropyranyl group of the formula

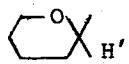

then removing the 4′,6′-hydroxyl-protecting group Y from the protected derivative of the formula (IV″) or (IV‴) in a known manner, and sulfonylating or halogenating the liberated 6′-hydroxyl group to prepare a 6′-sulfonyl or 6′-halo derivative of the formula:

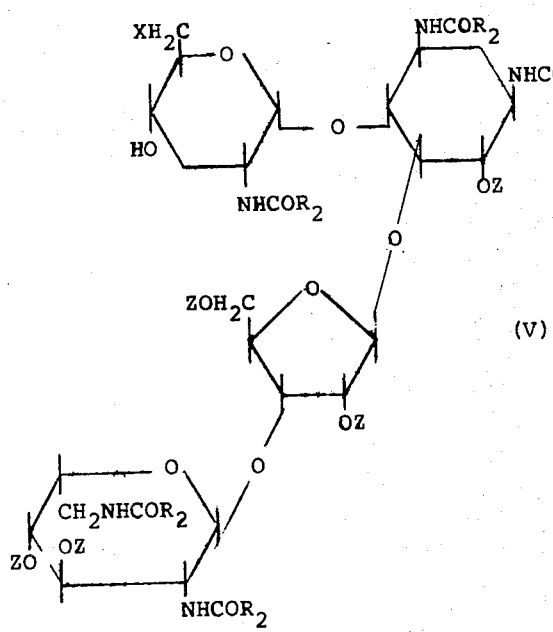

or of the formula:

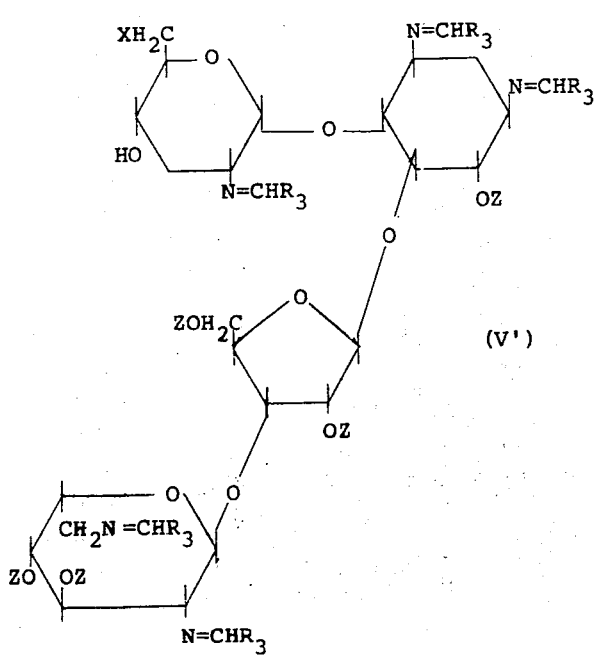

wherein $R_2$, $R_3$ and Z have the same meanings as defined above; and X is an alkylsulfonyl group (for example, an alkylsulfonyl of 1–4 carbon atoms such as methylsulfonyl or ethylsulfonyl) or an arylsulfonyl group (for example, phenylsulfonyl or p-tolylsulfonyl) or a halo group such as chloro, bromo or iodo group, and then converting the 6′-sulfonyl or 6′-halo group of the derivative of the formula (V) or (V′) into an amino group R as defined above in a known manner, and removing the remaining protective groups to produce the desired 6′-deoxy-6′-substituted or unsubstituted amino-lividomycin B of the formula (I).

In the second aspect process of the present invention, all the amino groups of the starting lividomycin B compound (II) is at first protected or blocked by acylating, alkoxycarbonylating, aryloxycarbonylating, arylmethoxycarbonylating, alkylidenating or arylidenating the amino groups with a known reagent which is commonly used in the usual synthesis of peptides to provide a known amino-protecting group of the type —$COR_2$ or of the type =$CHR_3$ wherein $R_2$ and $R_3$ are as defined hereinbefore.

In acylating the amino groups of the starting compound (II), the starting compound may be reacted in a known manner with a carboxylic acid of the type $HOOCR_2$ wherein $R_2$ is an alkyl group of 1-6 carbon atoms or an aryl such as phenyl, or a known reactive derivative of said carboxylic acid such as acyl halide or anhydride, in a solvent such as aqueous dioxane. Preferred acylating agents for this purpose includes acetyl chloride and benzoyl chloride. In alkyloxycarbonylating, aryloxycarbonylating or arylmethoxycarbonylating the amino groups of the starting compound (II), the starting compound may be reacted with a chloroformate of the formula:

or a p-nitrophenyl carbonate of the formula:

or an N-hydroxysuccinimide ester of the formula:

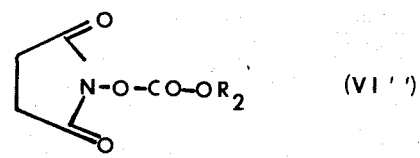

or an azidoformate of the formula:

in which $R_2$ is an alkyl group, an aryl group or an arylmethyl group, in a suitable solvent such as water, ethanol, acetone, or a mixture thereof under neutral or basic conditions in a manner known in the prior art of peptide synthesis. In alkylidenating or arylidenating the amino groups of the starting compound (II), the starting compound may be reacted with an aldehyde of the formula:

wherein $R_3$ is as defined above, in a manner known in the production of Schiff bases, to protect the amino groups with the protective group =CHR₃. Suitable alkylidenating or arylidenating agents for this purpose include acetaldehyde, anisaldehyde, tolualdehyde, p-nitrobenzaldehyde and salicyl aldehyde.

After the amino groups of the starting compound (II) are protected by the amino-protecting group to prepare the penta-N-protected lividomycin B derivative (III) or (III'), both the 4'-hydroxyl and 6'-hydroxyl groups of the derivative (III) or (III') are protected simultaneously by acetalation or ketalation, for example, by cyclohexylidenating, tetrahydropyranylidenating, alkylidenating or arylidenating these hydroxyl groups in a known manner such that the 4'- and 6'-hydroxyl groups are blocked simultaneously by a single divalent protective group —Y— as defined in the above. Suitable cyclohexylidenating, tetrahydropyranylidenating, alkylidenating or arylidenating agents for this purpose include 1,1-dimethoxycyclohexane, 1,1-dimethoxytetrahydroyrane, 2,2'-dimethoxypropane, anisaldehyde, benzaldehyde dimethyl acetal, and tolualdehyde diethyl dithioacetal. The agent may preferably be reacted with the amino-protected derivative (III) or (III') of the starting compound (II) in a suitable organic solvent such as dimethylformamide at a temperature of up to 100°C in the presence of a catalytic amount of an acid such as sulfuric acid and p-toluenesulfonic acid under anhydrous conditions, or under the action of mercuric chloride in case of agents containing a dithioacetal group.

After the 4',6'-O-protected derivative (IV) of (IV') is prepared in the above-mentioned way, all or part (but at least the 5''-hydroxyl group) of the remaining free hydroxyl groups are protected by acylation, benzylation or tetrahydropyranylation to produce the protected derivative (IV'') or (IV'''). Preferably, all the remaining free hydroxyl groups are protected by acylation. To this end, a carboxylic acid of the aforesaid tytpe HOOCR₁ or a known reactive derivative of this acid such as acyl halide or anhydride may be used as the acylating agent. The acylation for this purpose may be carried out in a basic medium such as pyridine at ambient temperature. Preferred acylating agents, for this purpose are acetyl chloride, acetic anhydride or benzoyl chloride. The benzylation may conveniently be conducted using benzyl halide in a usual manner. The tetrahydropyranylation of the remaining hydroxyl groups may be conducted using 3,4-dihydro-2H-pyrane

in a usual manner known in the art of protection of the functional hydroxyl group.

After the protection of the remaining hydroxyl groups is achieved, the removal of the 4',6'-hydroxyl-protecting group -Y- from the protected derivative (IV'') or (IV''') should be effected in the process of the present invention. The 4',6'-O-cyclohexylidene, tetrahydropyranylidene, alkylidene or arylidene group as the group —Y— may be removed selectively by subjecting to a mild hydrolysis in acetone or a lower alkanol such as methanol or ethanol containing a low concentration of a weak acid such as acetic acid or diluted hydrochloric acid, while the other hydroxy-protecting group is retained in the molecule of the protected derivative (IV'') or (IV'''). In this way, the 6'-hydroxyl group is liberated as well as the 4'-hydroxyl group. The 6'-hydroxyl group has a higher reactivity to sulfonylation or halogenation than the 4'-hydroxyl group, so that the 6'-hydroxyl group can be sulfonylated or halogenated preferentially to the 4'-hydroxyl group during the subsequent step of preparing the 6'-sulfonyl or 6'-halo derivative (V) or (V') in the process of the present invention.

The sulfonylation of the 6'-hydroxyl group so liberated may be carried out using a sulfonylating agent of the formula:

or

wherein R₄ is an alkyl group, particularly an alkyl group of 1–4 carbon atoms, or an aryl group, particularly benzyl, phenyl and p-tolyl; are A is a halogen atom, particularly chlorine or bromine, to prepare a 6'-sulfonyl derivative (V) or (V') where X stands for an alkylsulfonyl or arylsulfonyl group. Preferential alkylsulfonylation of the 6'-hydroxyl group to prepare the 6'-sulfonyl derivative (V) or (V') may preferably be achieved in such a way that the protected derivative containing the liberated 6'-hydroxyl group is reacted with an alkylsulfonylating agent of the formula:

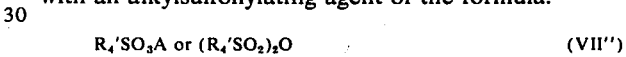

wherein R₄' is an alkyl group preferably of 1–4 carbon atoms and A is a halogen atom, a proportion of in less than 5 moles in a basic solvent such as pyridine or picolin at a temperature of up to about 50°C for a period of 1–24 hours. Preferential benzylsulfonylation or arylsulfonylation of the 6'-hydroxyl group may preferably be achieved in such a manner the protected derivative containing the liberated 6'-hydroxyl group is reacted with a benzylsulfonylating or an arylsulfonylating agent of the formula:

wherein R₄'' is an aryl group such as benzyl, phenyl, p-tolyl or p-bromophenyl and A is a halogen atom, in a basic solvent such as pyridine or picolin at a temperature of up to 50°C for a period of 1 to 24 hours. The benzylsulfonylating or arylsulfonylating agent of the formula (VII''') may be used in a proportion of less than 5 moles for 1 mole of the protected derivative of lividomycin B.

The halogenation, particularly chlorination or bromination of the liberated 6'-hydroxyl group, may be accomplished in an aprotic solvent such as dimethylformamide using a chlorinating or brominating agent such as thionyl chloride, thionyl bromide, phosphorous tribromide, phosphorous oxychloride and methanesulfonyl chloride or bromide and other related reagents. Among them, methanesulfonyl chloride or bromide is a most common chlorinating or brominating reagent with which a primary hydroxyl group may be halogenated selectively as described in a published literature e.g. see Evans, Long and Parrish, "Journal of Chemical Society" (London) Vol. 34, page 1627 (1966).

The 6'-sulfonyl or 6'-halo derivative (V) or (V') so prepared is then treated so as to convert its 6'-sulfonyl or 6'-halo group X into an amino group R as defined hereinbefore. When the derivative (V) or (V') is treated with a metal azide, preferably an alkali metal azide such as sodium azide, and potassium azide in an anhydrous organic solvent such as dimethylformamide at an elevated temperature of 40°C to 120°C, the 6'-sulfonyl or 6'-halo is replaced by the azide group $-N_3$, which is then reduced into the amino group $-NH_2$ by catolytic hydrogenation in the presence of a platinum metal such as platinum or palladium or Raney nickel as the hydrogenation catalyst. Alternatively, the derivative (V) or (V') may be treated immediately with ammonia or an alkylamine of the formula $R_1NH_2$ in an organic solvent such as a lower alkanol, for example methanol or ethanol, at an elevated temperature of up to the boiling point of the solvent used, or up to about 150°C in a pressure tube, so that the 6'-sulfonyl or 6'-halo group is converted directly into amino group $-NH_2$ or into a substituted amino group $-NHR_1$ where $R_1$ is as defined hereinbefore. The alkylamine $R_1NH_2$ may be methylamine, ethylamine, propylamine, butylamine or ethanolamine.

In the present process, there is produced an amino-protected and hydroxy-protected derivative of the 6'-deoxy-6'-amino-lividomycin B, from which the residual amino-protecting groups and the residual hydroxyl-protecting groups are removed in the final step of the present process. The removal of the amino-protecting groups and the hydroxyl-protecting groups which are remaining in the abovementioned protected 6'-deoxy-6'-amino derivative may be achieved in the following known different ways. Thus, when the amino-protecting group is e.g. an acyl group, an alkyloxycarbonyl group or an aryloxycarbonyl group, the removal of this kind of amino-protecting group may be effected by subjecting the protected 6'-deoxy-6'-amino derivative to an alkaline treatment with a base such as aqueous sodium hydroxide or aqueous barium hydroxide. When the amino-protecting group is an arylidene or alkylidene group, the removal of this kind of amino-protecting group may be effected by subjecting the protecting 6'-deoxy-6'-amino derivative to a moderate hydrolysis treatment with an acid such as aqueous trifluoroacetic acid, aqueous acetic acid or dilute hydrochloric acid. When the amino-protecting group is an arylmethoxycarbonyl group such as benzyloxycarbonyl, the removal of this sort of aminoprotecting group may be effected by subjecting the protected 6'-deoxy-6'-amino derivative to a hydrogenolysis treatment in the presence of a palladium catalyst or a to an alkaline treatment as described above. When the hydroxyl-masking group is of the acyl type such as alkanoyl and aroyl, the removal of this type of hydroxyl-masking group may be accomplished by alkaline hydroxide using aqueous sodium hydroride, ammonia in methanol or sodium methylate in methanol. When the hydroxyl-masking group is isopropylidene, cyclohexylidene, benzylidene, tetrahydropyranyl or methoxycyclohexyl, the removal of this type of hydroxyl-masking group may be accomplished by mild hydrolysis using dilute hydrochloric acid or aqueous acetic acid. However, occassionally the hydroxyl-masking groups of the acyl type can partially be removed at the same time as the removal of an amino-masking group of a similar acyl type is effected. When the hydroxyl-masking group is aryl such as benzyl, the removal of this type of hydroxyl-masking group may be achieved by catalytic hydrogenolysis in the presence of palladium on carbon.

In the process of the present invention, it is also possible to remove the hydroxyl-protecting group of the acyl type and/or the amino-protecting group of the acyl type immediately after the 6'-sulfonyl or 6'-halo group X of the derivative (V) or (V') is converted into the azide group $-N_3$ under the action of a metal azide but before the resultant 6'-azide group is reduced to an amino group. When catalytic hydrogenation of the 6'-azide group with hydrogen is effected, it may happen that the amino-protecting group of the arylmethoxycarbonyl type such as benzyloxycarbonyl and the hydroxyl-protecting group of the benzyl type are removed at the same time through hydrogenolysis.

In an event removal of the residual aminoprotecting groups and the residual hydroxyl-protecting groups from the above-mentioned protected 6'-amino-6'-amino derivative of lividomycin B gives the desired compound of the formula (I).

The invention is now illustrated with reference to the following Examples to which the invention is not limited in any way.

EXAMPLE 1

Synthesis of 6'-amino-6'-deoxylividomycin B (a) Preparation of penta-N-benzyloxycarbonyl-lividomycin B [in the formula (III): $R_2 = OCH_2C_6H_5$].

3.18 Grams of lividomycin B in the free base form, see the "Journal of Antibiotics" Vol. 25, pages 149–150 (1972), and 3.18 g of sodium carbonate were suspended in 100 ml of methanol. The suspension was admixed with 4.68 g of benzyloxycarbonyl chloride under cooling with ice and sodium chloride, and the mixture was then stirred for 3 hours under ice-cooling. The reaction mixture was concentrated to dryness and the residue was taken up into chloroform. The solution was washed with water and the solvent was distilled off. Reprecipitation of the residue from chloroform ethyl ether gave 5.86 g of a colorless powder which was identified as the above titled compound. $[\alpha]_D^{18} +40°$ (c 1.13, chloroform).

Elemental analysis. Found: C, 59.05; H, 5.82; N 5.34%. Calculated for $C_{63}H_{75}N_5O_{23}$: C, 59.57; H, 5.95; N 5.51%.

Preparation of 4',6'-O-benzylidene-penta-N-benzyloxycarbonyllividomycin B [in the formula (IV): $R_2 = OCH_2C_6H_5$, $Y = C_6H_5CH$].

Penta-N-benzyloxycarbonyllividomycin B (5.4 g) prepared by the above procedure (a) was dissolved in dry dimethyl formamide (100 ml) and the solution, after addition of benzaldehyde dimethyl acetal (7.2 ml) and anhydrous p-toluenesulfonic acid (136 mg), was heated at 30°–35°C for 3 hours under reduced pressure of 10–15 mm Hg and under stirring. The reaction mixture, after addition of 100 ml of anhydrous methanol, was allowed to stand at room temperature overnight. The reaction mixture was then neutralised by adding 3 ml of a saturated aqueous solution of sodium hydrogen carbonate thereto, and the mixture was concentrated to dryness. The residue was dissolved in chloroform and the solution was washed with water. The solvent was distilled off and the residue was taken up into and re-precipitated from chloroform ethyl ether, affording 5.5 g of a colorless powder which was identified as the above titled compound $[\alpha]_D^{18} +47.1°$ (c 0.85, chloroform).

Elemental analysis. Found: C, 61.59; H, 5.77; N, 5.11%. Calculated for $C_{70}H_{79}N_5O_{23}$: C, 61.89; H, 5.86; N, 5.16%.

Preparation of penta-O-acetyl-4',6'-O-benzylidene-penta-N-benzyloxycarbonyllividomycin B [in the formula (IV''): $R_2 = OCH_2C_6H_5$, $Y = C_6H_5CH$, $Z = COCH_3$].

4',6'-O-benzylidene-penta-N-benzyloxycarbonyl-lividomycin B (1.36 g) prepared in the above procedure (b) was dissolved in pyridine (30 ml) and the solution, after addition of acetic anhydride (6 ml), was stirred at room temperature overnight to effect the acetylation. The reaction mixture was concentrated and the residue was dissolved in chloroform. The solution was washed with water and then evaporated to remove the solvent. A white colored powder (1.5 g) was afforded, which was identified as the above titled compound. $[\alpha]_D^{14}$ +21° (c 1, chloroform).

Elemental analysis Found: C, 61.19; H, 5.83; N 4.43%. Calculated for $C_{80}H_{89}N_5O_{28}$: C, 61.26; H, 5.72; N 4.46%.

(d) Preparation of penta-O-acetyl-penta-N-benzyloxycarbonyllividomycin B [in the formula (V): $R_2 = OCH_2C_6H_5$, $X = OH$, $Z = COCH_3$].

The lividomycin B derivative (1.45 g) prepared in the above procedure (c) was dissolved in a liquid mixture of 15 ml of acetone, 30 ml of acetic acid and 15 ml of water, and the solution was reacted at 60°C for 3 hours to effect the removal of the benzylidene group. The reaction mixture was concentrated under reduced pressure to dryness and the solid residue was taken up into chloroform. The solution was washed with water and the solvent was evaporated off, affording 1.26 g of a white colored powder. Yield 94 percent. This material was identified as the above titled compound. $[\alpha]_D^{14}$ +23° (c 1, chloroform).

Elemental analysis. Found: C, 59.18; H, 5.67; N, 4.80%. Calculated for $C_{73}H_{85}N_5O_{28}$: C, 59.22; H, 5.79; N, 4.73%.

(e) Preparation of penta-O-acetyl-penta-N-benzyloxycarbonyl-6'-O-tosyl-lividomycin B [in the formula (V): $R_2 = OCH_2C_6H_5$, $X = OSO_2C_6H_5CH_3$, $Z = COCH_3$].

The lividomycin B derivative (960 mg) prepared in the above procedure (d) was dissolved in 20 ml of anhydrous pyridine and the solution was cooled to −10°C. The solution, after addition of 625 mg of p-toluene-sulfonic chloride, was allowed to stand at the same temperature overnight. The reaction mixture was admixed with 0.3 ml of water and the solution was then concentrated by evaporation of the solvent under reduced pressure. The residue was taken up into chloroform and the solution was washed with water and the solvent was distilled off, affording a white colored powder (1.0 g). This material was identified as the above titled compound. $[\alpha]_D^{14}$ +29.5° (c 0.34, chloroform).

Elemental analysis. Found: C, 58.95; H, 5.41; N, 4.34; S, 2.11%. Calculated for $C_{80}H_{91}N_5O_{30}S$: C, 58.78; H, 5.61; N, 4.28, S, 1.96%.

(f) Production of penta-O-acetyl-6'-azide-penta-N-benzyloxycarbonyl-6'-deoxylividomycin B [in the formula (V): $R_2 = OCH_2C_6H_5$, $X = N_3$, $Z = COCH_3$].

The lividomycin B derivative (500 mg) prepared in the above procedure (e) was dissolved in 12.5 ml of anhydrous dimethyl formamide and the solution, after addition of 200 mg of sodium azide, was stirred at 60°C for 4 hours. After addition of 100 ml of chloroform, the solution was washed three times with saturated aqueous solution of sodium chloride and then three times with water, and was subsequently dried over anhydrous sodium sulfate. The distillation of the solvent from the solution gave a solid residue which was then dissolved in and precipitated from benzene-n-hexane. The above titled compound was obtained in a yield of 435 mg (95%). $[\alpha]_D^{16}$ +27.5° (c 1, chloroform).

Elemental analysis. Found: C, 58.10; H, 5.70; N, 7.41%. Calculated for $C_{73}H_{84}N_8O_{27}$: c. 58.24; H, 5.62; N, 7.44%.

Production of 6'-amino-6'-deoxylividomycin B [in the formula (I): $R = NH_2$].

The lividomycin B derivative (360 mg) produced in the above procedure (f) was dissolved in 15 ml of 5% ammoniac methanol and the solution was allowed to stand at room temperature overnight to effect the removal of the acetyl groups. The reaction mixture was then concentrated by evaporation of the solvent and the residue so obtained was dissolved in chloroform. The solution was washed with water and the solvent distilled off. The resulting residue (300 mg) was taken up into a mixture of 4.5 ml of dioxane, 0.3 ml of glacial acetic acid and 2.2 ml of water, and the solution, after addition of 0.03 g of palladium black, was subjected to hydrogenation with hydrogen at a pressure of 3 atm to effect the reduction of the azide group and the removal of the benzyloxycarbonyl groups. The reaction mixture was filtered and then concentrated. The residue was dissolved in water and the aqueous solution was chromatographed in a column of a weak cation-exchanger essentially consisting of a three-dimensional network gel of dextran bearing carboxymethyl radicals as the weakly cationexchanger functions (a product of Pharmacia Co., Sweden, sold under a trade name "CM-Sephadex C-25", $NH_4^+$ form) by developing with aqueous ammonia while increasing the ammonia concentration from 0 to 0.3 N. The active fractions containing the desired compound were collected and concentrated to give a colorless powder in a yield of 110 mg. This substance gave a single spot of Rf 0.5 (assumed that the free base of lividomycin B showed Rf 1.0) when it was subjected to paper chromatography using (6:4:3:1) n-butanol-pyridine-water-acetic acid as the developing solvent. $[\alpha]_D^{15}$ +52° (c 1, water).

Elemental analysis. Found: C, 44.57; H, 7.98; N, 13.93%. Calculated for $C_{23}H_{46}N_6O_{12}\cdot H_2O$: C, 44.80; H, 7.86; N, 13.63%.

EXAMPLE 2

Synthesis of 6'-methylamino-6'-deoxylividomycin B [in the formula (I): $R = NHCH_3$]

Penta-O-acetyl-penta-N-benzyloxycarbonyl-6'-O-tosyllividomycin B (500 mg) prepared in the procedure of Example 1 (e), was dissolved in 10 ml of methanol containing 30% methylamine, and the mixture was stirred at 50°C for 5 hours to effect the reaction in which the 6'-tosyl group was replaced by 6'-methylamino group. The reaction mixture was concentrated and the residue was taken up into chloroform. The solution was washed with water and dried over anhydrous sodium sulfate and then concentrated to dryness. The white colored powder so obtained (360 mg) was then dissolved in a mixture of 5 ml of dioxane and 2 ml of water and then hydrogenated with hydrogen in the presence of 0.04 g of palladium black added, so that the residual amino-protecting and hydroxyl-protecting groups were removed. The reaction mixture was filtered concentrated, the residue was dissolved in water and the aqueous solution was chromatographed in a column of CM-Sephadex C-25 ($NH_4^+$ form) using aqueous ammonia with increasing the ammonia concentrations from 0 to 0.3 N. The active fractions containing the desired compound were collected and concentrated, giving 120 mg of a colorless powder which was identified as the above titled compound. $[\alpha]_D^{15}$ +48° (c 1, water). NMR (in $D_2O$): $\tau$ 7.23 (3H singlet, N—$CH_3$).

Elemental analysis. Found: C, 45.61; H, 8.21; N, 13.48%. Calculated for $C_{24}H_{48}N_6O_{12}\cdot H_2O$: C, 45.70; H, 7.99; N, 13.32%.

EXAMPLE 3

Synthesis of 6'-deoxy-6'-(2-hydroxyethylamino)-lividomycin B [in the formula (I): R = $NHCH_2CH_2OH$].

Penta-O-acetyl-penta-N-benzyloxycarbonyl-6'-O-tosyllividomycin B (100 mg) prepared in the procedure of Example 1 (e) was dissolved in 1.8 ml of methanol, and the solution was admixed with 0.25 ml of ethanolamine. The mixture was heated at 50°C for 40 hours in a sealed tube, and the reaction mixture was concentrated and the residue was dissolved in chloroform. The solution was washed with water, dried over anhydrous sodium sulfate and then concentrated to dryness, affording a white colored powder. The powder was subsequently processed in the same manner as in Example 2 to give 15 mg of a colorless powder, which was identified as the above titled compound. $[\alpha]_D^{20}$ +63° (c 1, water).

Elemental analysis. Found: C, 45.34; H, 7.83; N, 12.55%. Calculated for $C_{25}H_{50}N_6O_{13}\cdot H_2O$: C, 45.45; H, 7.93; N, 12.72%.

EXAMPLE 4

(a) Preparation of penta-O-acetyl-penta-N-benzyloxycarbonyl-6'-bromo-6'-deoxylividomycin B [in the formula (V): $R_2$ = $OCH_2C_6H_5$, X = Br, Z = $COCH_3$].

Penta-O-acetyl-penta-N-benzyloxycarbonyllividomycin B (180 mg) prepared in the procedure of Example 1 (d) was dissolved in 4 ml of anhydrous dimethylformamide and the solution, after addition of 28 mg of methanesulfonyl bromide, was stirred at room temperature for 10 hours to effect the 6'-bromination. The reaction mixture was concentrated under reduced pressure and the residue was dissolved in chloroform. The solution was washed with water, dried over anhydrous sodium sodium. sulfate and then distilled to remove the solvent. A colorless powder was given in a yield of 175 mg and was identified as penta-O-acetyl-penta-N-benzyloxycarbonyl-6'-bromo-6'-deoxylividomycin B. $[\alpha]_D^{18}$ +28° (c 1, chloroform).

Elemental analysis. Found: Br, 5.30%. Calculated for $C_{73}H_{84}N_5O_{27}Br$: Br, 5.19%.

(b) Preparation of penta-O-acetyl-6'-azide-penta-N-benzyloxycarbonyl-6'-deoxylividomycin B [in the formula (V): $R_2$ = $OCH_2C_6H_5$, X = $N_3$, Z = $COCH_3$].

The protected 6'-bromo derivative of lividomycin B prepared in the above procedure of Example 4 (a) was treated in the same manner as in Example 1 (f). The above titled compound was obtained.

EXAMPLE 5.

Synthesis of 6'-amino-6'-deoxylividomycin B (a) Preparation of penta-N-p-methylbenzylidene-4', 6'-O-p-methylbenzylidene-lividomycin B [in the formula (IV'): $R_3$ = $C_6H_4CH_3$, Y = $CHC_6H_4CH_3$].

To a suspension of lividomycin B base (380 mg) in 20 ml of a mixture of water and methanol (1:8), p-tolualdehyde (500 mg) was added and the resulting solution was then poured into water. The precipitate formed was filtered and dried to give 250 mg of a powder. This powder, identified as the penta-N-p-methylbenzylidenelividomycin B, was dissolved in dimethylformamide (20 ml) and the solution was admixed with tolualdehyde diethyl dithioacetal $CH_3C_6H_4CH(SC_2H_5)_2$ (500 mg), mercuric chloride (700 mg), anhydrous cadmium carbonate (500 mg) and a molecular sieve (Type 4A, Union Carbide Co., Ltd.), and the resultant suspension was agitated for 10 hours. The suspension was filtered and the filtrate was evaporated and the residue was dissolved in chloroform. The solution was washed with water containing potassium iodide, dried over anhydrous sodium sulfate and evaporated to give a solid which was identified as the above titled compound. Yield 230 mg.

(b) Preparation of penta-O-acetyl-penta-N-p-methylbenzylidene-4',6'-O-p-methylbenzylidenelividomycin B [in the formula (IV'''): $R_3$ = $C_6H_4CH_3$, Y = $CHC_6H_4CH_3$, Z = $COCH_3$].

The lividomycin B derivative (500 mg) prepared by the above procedure of Example 5 (a) was dissolved in pyridine (10 ml) and the solution was treated with acetic anhydride (500 mg) in a similar way to the procedure of Example 1 (c). After the reaction mixture was evaporated, the residue was dissolved in chloroform. The solution was washed with an aqueous solution of sodium hydrogen carbonate, dried over anhydrous sodium sulfate and evaporated to give a solid which was the above titled compound. Yield 565 mg.

(c) Production of penta-O-acetyl-penta-N-p-methylbenzylidene-6'-O-tosyllividomycin B [in the formula (V'): $R_3$ = $C_6H_4CH_3$, X = $OSO_2C_6H_4CH_3$, Z = $COCH_3$].

The lividomycin B derivative (1.2 g) prepared by the above procedure of Example 5 (b) was dissolved in a mixture of acetone (15 ml), acetic acid (30 ml) and water (15 ml), and the solution was heated at 60°C for 3 hours. The reaction mixture was evaporated to give a solid residue, which was dissolved in 30 ml of a mixture of water-methanol (1:8). To the solution so obtained were added sodium carbonate (1.0 g) and tolualdehyde (700 mg), and the resulting solution was poured into water. The precipitate formed was filtered out, washed with water and dried. The solid obtained was tosylated with p-toluenesulfonic chloride in a similar way to the procedure of Example 1 (e), to give the above titled compound. Yield 930 mg.

Elemental analysis Found: C, 65.33; H, 6.15; N, 4.53; S, 2.09%. Calculated for $C_{80}H_{91}N_5O_{20}S$: C, 65.16; H, 6.22; N, 4.75; S, 2.17%.

(d) Production of 6'-amino-6'-deoxylividomycin B

The protected 6'-tosyl derivative of lividomycin B (530 mg) prepared in the above procedure of Example 5 (c) was then dissolved in methanol (15 ml) saturated with ammonia and the mixture was refluxed for 5 hours, during which the replacement of the 6'-tosyl group by amino group as well as the removal of the acetyl groups and the p-methylbenzylidene groups took place. The reaction mixture was filtered and concentrated to dryness. The residue was dissolved in water and the aqueous solution was chromatographed in a column of CM-Sephadex C-25 ($NH_4^+$ form) in the same manner as in Example 1 (g), affording 110 mg of 6'-amino-6'-deoxylividomycin B.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages conditions.

What we claim is:

1. A 6'deoxy-6'-amino-lividomycin B compound of the formula:

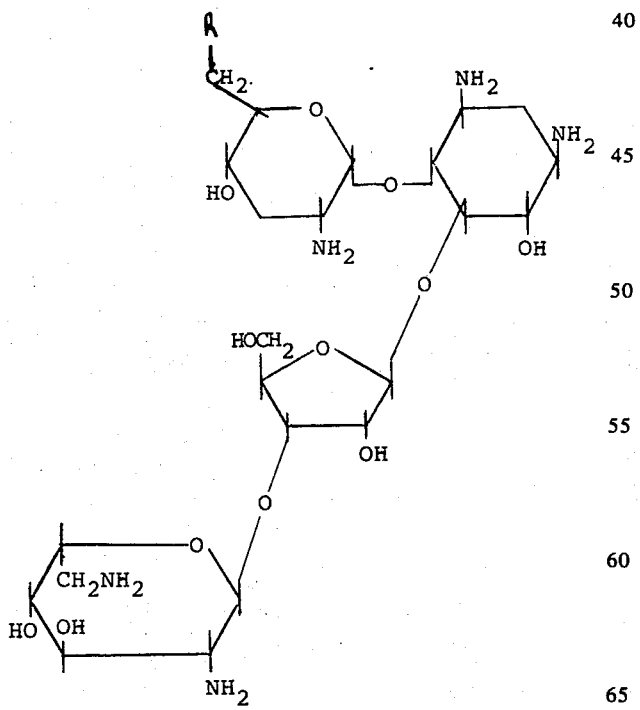

wherein R is amino, monoalkylamino of 1–4 carbon atoms or 2-hydroxyethylamino, or a pharmaceutically acceptable acid addition salt thereof.

2. A compound according to claim 1 wherein R is monoalkylamino of 1–4 carbon atoms, or a pharmaceutically acceptable acid addition salt thereof.

3. A compound according to claim 1, 6'-deoxy-6' methylaminolividomycin B or a pharmaceutically acceptable acid addition salt thereof.

4. A compound according to claim 1, 6'amino-6'-deoxylividomycin B or a pharmaceutically acceptable acid additional salt thereof.

5. A compound according to claim 1, 6'deoxy-6'-(2-hydroxyethylamino) lividomycin B or a pharmaceutically acceptable addition salt thereof.

6. A process for preparing a compound according to claim 1, which comprises:
  a. 6'-sulfonylating with a sulfonylating agent of the formula $R_4SO_3A$ or of the formula $(R_4SO_2)_2O$ wherein $R_4$ is alkyl of 1–4 carbon atoms, benzyl, phenyl, p-tolyl or p-bromophenyl and A is halogen or 6'-halogenating in an apropic solvent with a chlorinating or brominating agent the 6'-hydroxyl group of penta-N masked lividomycin B compound of the formula:

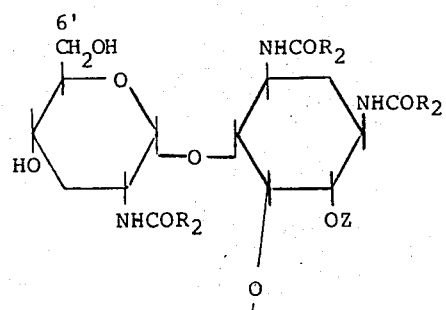

or of the formula:

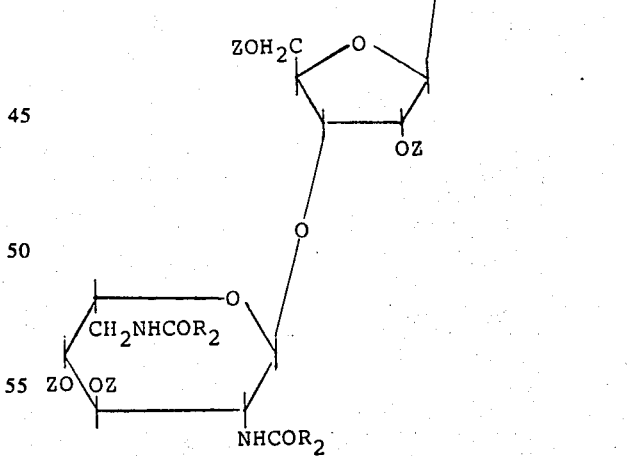

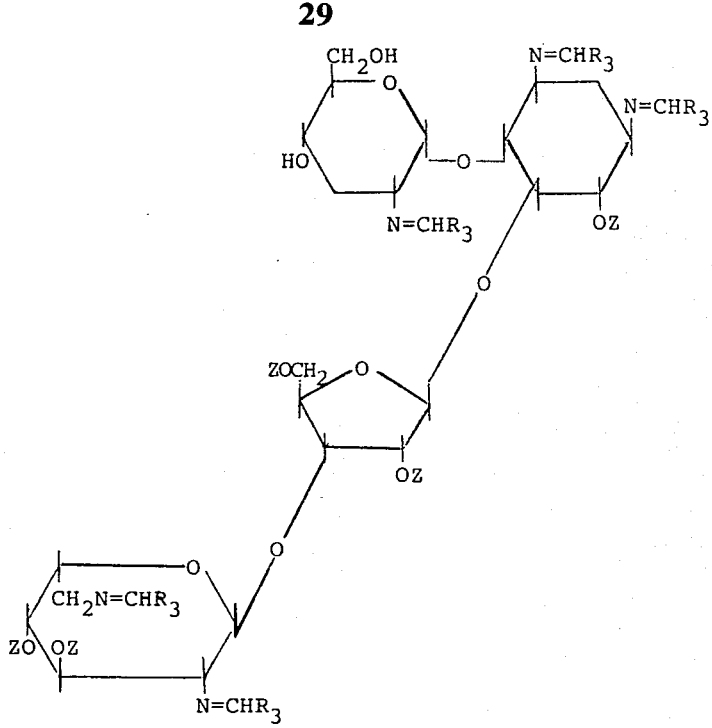

wherein

R₂ is hydrogen, alkyl of 1–4 carbon atoms, phenyl, alkoxy of 1-6 carbon atoms, phenoxy, benzyloxy or p-nitrobenzyloxy;

R₃ is alkyl of 1-6 carbon atoms, phenyl, tolyl, p-methoxyphenyl or o-hydroxyphenyl; and Z is hydrogen, alkanoyl of 2-5 carbon atoms, benzyl or tetrahydropyranyl to form a 6'-sulfonylated or 6'-halogenated derivative of said masked lividomycin B compound;

b. aminating the resultant 6'-sulfonic ester group or 6'-halo group by reacting said 6'-sulfonic ester or 6'-halo group with an alkali metal azide to form a corresponding 6'-azide and reducing said azide to the amino group by hydrogenation or by reacting said 6'-sulfonic ester or 6'-halo group in an organic solvent with ammonia or an alkylamine of the formula R₁NH₂ wherein R₁ has the above-indicated values to convert said 6' group to amino, monoalkylamino of 1–4 carbon atoms or 2-hydroxyethylamino; and c. reducing the hydroxyl protecting groups Z and the amino protecting groups R₂ and R₃ to hydrogen to form said 6'-deoxy-6'-amino-lividomycin B compound.

7. A process according to claim 6 wherein step a) comprises 6'-sulfonylating with less than 5 moles of sulfonylating agent per mole of said masked lividomycin B compound in a basic solvent at a temperature of up to about 50°C for 1-24 hours.

8. A process according to claim 6 wherein said 6'-azide is formed by reacting said masked lividomycin B derivative with an alkali metal azide in an anhydrous organic solvent at a temperature of 40°–120°C.

9. A process according to claim 6 wherein step b) comprises reacting said 6'-sulfonic ester or 6'-halo group in an organic solvent with ammonia or an alkylamine of the formula R₁NH₂ wherein R₁ has the above-indicated values.

* * * * *